US006479282B1

(12) United States Patent
Letourneur et al.

(10) Patent No.: US 6,479,282 B1
(45) Date of Patent: Nov. 12, 2002

(54) HBC EXPRESSION AND DIAGNOSTIC AND THERAPEUTIC USES

(75) Inventors: Odile Letourneur, Saint Foy les Lyon (FR); Bénédicte Watelet, Montpellier (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/851,120

(22) Filed: May 9, 2001

(51) Int. Cl.[7] .......................... C12N 15/00; C12Q 1/70; C12P 21/06; C12P 21/04; C07K 16/00
(52) U.S. Cl. .................. 435/320.1; 435/5; 435/69.1; 435/71.1; 530/388.3
(58) Field of Search ..................... 435/5, 69.1, 71.1, 435/320.1; 530/388.3

(56) References Cited

U.S. PATENT DOCUMENTS 4,963,483 A * 10/1990 Ellis et al. .................. 435/69.3

FOREIGN PATENT DOCUMENTS

| WO | WO 99/06837 A | 2/1999 |
| WO | WO 00/16802 A | 3/2000 |

OTHER PUBLICATIONS

D. Rolland et al., "Purification of recombinant HBc antigen expressed in *Eschericia coli* and *Pichia pastoris*: comparison of size–exclusion chromatography and ultracentrifugation", Journal of Chromatography B, 753, (2001), pp. 51–65.
G. Galfre al., "Antibodies to Major Histocompatibility Antigens Produced by Hybrid Cell Lines", Nature, vol. 266, Apr. 1977, pp. 550–552.
G.P. Borisova et al, "Recombinant core particles of hepatitis B virus exposing foreign antigenic determinants on their surface", FEBS Letters, vol. 259, No. 1, pp. 121–124, Dec. 1989.

Fumiko Arakawa et al., "Cloning and Sequencing of the $V_H$ and $V_k$ Genes of an Anti–CD3 Monoclonal Antibody, and Construction of a Mouse/Human Chimeric Antibody", J. Biochem, vol. 120, No. 3, pp. 657–662, 1996.
David R. Milich et al., "Role of B cells in antigen presentation of the hepatitis B core", Proc. National Academy of Sciences USA, vol. 94, pp. 14648–14653, Dec. 1997.
G. Kohler et al., "Continuous cultures of fused cells secreting antibody of predefined specificity", Nature, vol. 256, pp. 495–497, Aug. 1975.
Valerie Cheynet et al., "Overexpression of HIV–1 Proteins in *Escherichia coli* by a Modified Expression Vector and Their One–Step Purification", Protein Expression and Purification vol. 4, pp. 367–372, 1993.
B.J. Cohen et al., "Electron microscopy of hepatitis B core antigen synthesized in *E. coli*", Nature, vol. 296, pp. 677–678, Apr. 15, 1982.
Albrecht von Brunn et al., "Principal neutralizing domain of HIV–1 is highly immunogenic when expressed on the surface of hepatitis B core particles", Vaccine, vol. 11, Issue 8, pp. 817–824, 1993.

(List continued on next page.)

Primary Examiner—Hankyel T. Park
(74) Attorney, Agent, or Firm—Oliff & Berridge, PLC

(57) ABSTRACT

A cassette that functions in yeast cells allowing and controlling expression of HBc Ag, HBc Ag fragments and/or recombinant HBc Ag; a reagent for detection and/or monitoring of HBV infections that relies on a product of the cassette; processes for producing monoclonal and/or polyclonal antibodies to the product of the cassette; and processes for (1) diagnosis, (2) vaccine production, (3) vaccination, (4) pharmaceutical production and (5) treatment that rely on the product of the cassette and/or the monoclonal and/or polyclonal antibodies to the product of the cassette.

19 Claims, 4 Drawing Sheets

OTHER PUBLICATIONS

A. Roda et al., "Production of a High-Titer Antibody to Bile Acids", Journal of Steriod Biochemistry, vol. 13, pp. 449–454, 1980.

David R. Milich et al., "The Hepatitis B Virus Core and e Antigens Elicit Different Th Cell Subsets: Antigen Structure Can Affect Th Cell Phenotype", Journal of Virology, vol. 71, No. 3, pp. 2192–2201, Mar. 1997.

Andrea Gallina et al., "A Recombinant Hepatitis B Core Antigen Polypeptide with the Protamine–Like Domain Deleted Self–Assemblies into Capsid Particles but Fails To Bind Nucleic Acids", Journal of Virology, vol. 63, No. 11, pp. 4645–4652, Nov. 1989.

Vijay K. Chaudhary et al., "A recombinant immunotoxin consisting of two antibody variable domains fused to Pseudomonas exotoxin", Nature, vol. 339, pp. 394–397, Jun. 1989.

B. Bottcher et al., "Determination of the fold of the core protein of hepatitis B virus by electron cryomicroscopy", Nature, vol. 386, pp. 88–91, Mar. 1997.

Frank Birnbaum et al., "Hepatitis B Virus Nucleocapsid Assembly: Primary Structure Requirements in the Core Protein", Journal of Virology, vol. 64, No. 7, pp. 3319–3330, Jul. 1990.

Robert E. Bird et al., "Single–Chain Antigen–Binding Proteins", Science, vol. 242, pp. 423–426, Oct. 1988.

Jian Zheng et al., "The Structure of Hepadnaviral Core Antigens", The Journal of Biological Chemistry, vol. 267, No. 13, pp. 9422–9429, 1992.

Siliang Zhou et al., "Cys Residues of the Hepatitis B Virus Capsid Protein Are Not Essential for the Assembly of Viral Core Particles but Can Influence Their Stability", Journal of Virology, vol. 66, No. 9, pp. 5393–5398, Sep. 1992.

S. A. Wynne et al., "The Crystal Structure of the Human Hepatitis B Virus Capsid", Molecular Cell, vol. 3, pp. 771–780, Jun. 1999.

H. Wizemann et al., "Purification of the E. coli–expressed HIS–tagged hepatitis B core antigen by $Ni_{2+}$ –chelate affinity chromatography", Journal of Virological Methods vol. 77, pp. 189–197, 1999.

Paul T. Wingfield et al., "Hepatitis Core Antigen Produced in Escherichia coli: Subunit Composition, Conformational Analysis, and In Vitro Capsid Assembly", Biochemistry, vol. 34, No. 15, pp. 4919–4932, 1995.

John A. Weare et al., "Improvement in the Specificity of Assays for Detection of Antibody to Hepatitis B Core Antigen", Journal of Clinical Microbiology, vol. 29, No. 3, pp. 600–604, Mar. 1991.

Eugene F. Robertson et al., "Characterization of a Reduction–Sensitive Factor from Human Plasma Responsible for Apparent False Activity in Competitive Assays for Antibody to Hepatitis B Core Antigen", Journal of Clinical Microbiology, vol. 29, No. 3, pp. 605–610, Mar. 1991.

J. Salfeld et al., "Antigenic Determinants and Functional Domains in Core Antigen and e Antigen from Hepatitis B Virus", Journal of Virology, vol. 63, No. 2, pp. 798–808, Feb. 1989.

Adrian M. Spronk et al., "Improvements in Detection of Antibody to Hepatitis B Core Antigen by Treating Specimens with Reducing Agent in an Automated Microparticle Enzyme Immunoassay", Journal of Clinical Microbiology, vol. 29, No. 3, pp. 611–616, Mar. 1991.

Pablo Valenzuela et al., "The Nucleotide Sequence of the Hepatitis B Viral Genome and the Identification of the Major Viral Genes", Animal Virus Genetics, pp. 57–70, 1980.

Kang–Xian Luo et al., "Hepatitis B Virus DNA in Sera of Virus Carriers Positive Exclusively for Antibodies to the Hepatitis B Core Antigen", Journal of Medical Virology, vol. 35, pp. 55–59, 1991.

A. Machida et al., "Phosphorylation in the Carboxyl–Terminal Domain of the Capsid Protein of Hepatitis B Virus: Evaluation with a Monoclonal Antibody", Journal of Virology, vol. 65, No. 1, pp. 6024–6030, Nov. 1991.

M. Naito et al., "Simple method for efficient production of hepatitis B virus core antigen Escherichia coli", Res. Virol., vol. 148, pp. 299–305, 1997.

Flor H. Pujol et al., "A Monoclonal Inhibition Enzyme Immunoassay for Detection of Antibodies Against Hepatitis B Core Antigen: Confirmation of an Immunodominant Epitope", Journal of Immunoassay, vol. 15, No. 3, pp. 239–249, 1994.

P. Pushko et al., "Identification of Hepatitis B Virus Core Protein Regions Exposed or Internalized at the Surface of HbcAg Particles by Scanning with Monoclonal Antibodies", Virology vol. 202, pp. 912–920, 1994.

Wayne Liao et al., "Phosphorylation and Nuclear Localization of the Hepatitis B Virus Core Protein: Significance of Serine in the Three Repeated SPRRR Motifs", Journal of Virology, vol. 69, No. 2, pp. 1025–1029, Feb. 1995.

Robert E. Lanford et al., "Expression of Hepatitis B Virus Core and Precore Antigens in Insect Cells and Characterization of a Core–Associated Kinase Activity", Virology, vol. 176, pp. 222–233, 1990.

John M. Kenney et al., "Evolutionary conservation in the hepatitis B virus core structure: comparison of human and duck cores", Structure, vol. 3, No. 10, pp. 1009–1019, 1995.

Larisa I. Karpenko et al., "Localization of the amino terminus of the hepatitis B Virus core antigen within the core particle", virus Research vol. 52, pp. 15–23, 1997.

R. Y. Dodd et al., "Antibodies to hepatitis B core antigen and the infectivity of the blood supply", Transfusion, vol. 31, No. 5, pp. 443–449, 1991.

R. A. Crowther et al., "Three–Dimensional Structure of Hepatitis B Virus Core Particles Determined by Electron Cryomicroscopy", Cell, vol. 77, pp. 943–950, Jun. 1994.

J. F. Conway et al., "Localization of the N terminus of hepatitis B virus capsid protein by peptide–based difference mapping from cryoelectron microscopy", Proc. Natl. Acad. Sci. USA, vol. 95, pp. 14622–14627, Dec. 1998.

Rolland, D. et al.: "Purification of recombinant HBc antigen expressed in Escherichia coli and Pichia pastoris: comparison of size–exclusion chromatography and ultracentrifugation," Journal of Chromatography B. vol. 753, 2001, pp. 51–65.

* cited by examiner

HBC EXPRESSION AND DIAGNOSTIC AND THERAPEUTIC USES

BACKGROUND OF THE INVENTION

Hepatitis B virus (HBV) is the most significant of the hepatotrophic viruses in terms of the number of people chronically infected and the severity of the complications of infection. It is a major cause of human liver disease which can lead to chronic infection, cirrhosis and hepatocellular carcinoma, resulting in over a million deaths worldwide each year.

HBV is a double stranded DNA virus that may be carried by as much as 20% or more of the apparently healthy population in certain parts of the world, such as Africa, Asia and the Pacific Region (Principles and Practice of Clinical Virology, 3rd Edition, Chapter 2: Hepatitis Viruses, pp. 162–180). The reservoir of carriers worldwide is estimated at a number over 300 million. HBV was originally thought to be spread exclusively by blood and blood products, although it now appears that HBV can also be transmitted by intimate contact, such as sexual contact, and other routes may also be possible. Thus, transmission of infection may result from accidental inoculation of minute amounts of blood, or fluid contaminated with blood, during medical, surgical and dental procedures; immunization with inadequately sterilized syringes and needles; intravenous or percutaneous drug abuse; tatooing; ear, nose and other piercing; acupuncture; laboratory accidents; and, accidental inoculation with razors and similar objects that have been contaminated with blood.

The genomes of a variety of isolates of HBV have been cloned and the complete nucleotide sequence thereof determined. Although there is some variation in sequence (up to about 12% of nucleotides) between these isolates, the genetic organization and other essential features are conserved. The genome is around 3200 base pairs in length and analysis of the protein coding potential reveals four conserved ORFs. The four ORFs are located on the same DNA strand and the strands of the genome have accordingly been designated the plus (incomplete strand) and minus (complete strand).

HBV belongs to the hepadnaviridae family and consists of an outer envelope of host-derived lipids containing a virion-encoded surface antigen (HBsAg). This 42 nm lipoprotein shell encloses an icosahedral nucleocapsid assembled from the core antigen (HBcAg) that contains the viral genomic DNA and the viral polymerase (for review, see Nassal and Schaller, 1993). The core protein is the cytoplasmic product of the C-gene, composed of 183 or 185 amino acid residues (21 kDa) depending on sero-subtypes, which can be divided into an N-terminal assembly domain (residues 1–149) and a C-terminal very basic protamine-like domain (residues 150–185), respectively responsible for polymerization into particles and RNA packaging. The HBc protein has the ability to form disulfide-linked homodimers which spontaneously assemble into particles (Zhou and Standring, 1992).

HBcAg is a very powerful immunogen inducing strong humoral, T helper (Th) and cytotoxic T cell (CTL) responses and functioning as both T-cell-dependent and T-cell-independent antigen (Milich et al., 1997a, b). Anti-HBc arise in virtually all infected individuals. They are produced very early after infection and may be detected a few days after the detection of HBsAg in the blood of infected subjects. Moreover, in acute infections, HBsAg declines over a period of several weeks and is replaced by detectable levels of HBsAg antibody (anti-HBs). During a "window" period, when neither HBsAg nor its homologous antibody is detectable, anti-HBc may be the only detectable serological marker of HBV infection. In addition, anti-HBc usually persists longer than any other HBV marker. Anti-HBc is therefore the most useful marker for the diagnosis of an ongoing or past HBV infection and for epidemiological purposes.

Intensive studies have shown that HBcAg can be produced in a variety of heterologous expression systems including E. coli and undergoes correct folding and self-assembly to form core particles similar to native capsids (Pasek et al., 1979; Cohen and Richmond, 1982; Naito et al., 1997; Wizeman and von Brunn, 1999). Bacterially expressed HBc molecules assemble into particles of two sizes arranged respectively with a triangulation number T=3 (90 dimers) or T=4 (120 dimers) icosahedral symmetry (Crowther et al., 1994; Wingfield et al., 1995). The physiological implications of this dimorphic switch are not clear, although the T=4 form is reported to outnumber the T=3 form by ~13 to 1 in capsids isolated from the human liver (Kenney et al., 1995). The crystal structure of the T=4 capsid of the bacterially expressed truncated protein (aa .1–149) has been solved by X-ray crystallography to 3.3 Å resolution (Wynne et al., 1999). The monomer fold is characterized by four $\alpha$-helices and the absence of $\beta$-sheets. In agreement with previous biochemical analyses, the structural data revealed two regions required for the dimerization of core monomers and for the subsequent assembly of the dimers into core particles (Wynne et al., 1999).

Many different procedures have been described to purify HBcAg. Common purification procedures are based on sedimentation of the core particles on sucrose gradients which do not allow the removal of all contaminating E. coli material and are often associated with a low yield. As a consequence, most of the commercially available anti-HBc detection systems are immunoassays based on inhibition or competition where human anti-HBc inhibit a labeled anti-HBc from binding to an immobilized recombinant HBcAg (Pujol et al., 1994). Consequently, the presence of anti-HBc in the sample generates a low signal value, whereas its absence results in a high signal value. This conventional test format circumvents the need for highly purified HBcAg, but has potential drawbacks which include poor specificity and poor reproducibility especially near assay cutoff (Dodd and Popovsky, 1991). False-positive anti-HBc reactivity has been attributed to cross-reactive antibodies or interfering substances in human serum (Robertson et al., 1991). It has been shown that the pretreatment of serum samples with reducing agents could significantly improve the specificity of anti-HBc determination in competitive assay (Robertson et al., 1991; Spronk et al., 1991; Weare et al., 1991). However in order to avoid cost-intensive remeasurements in routine diagnosis and discarding of blood donations due to (false)-positive anti-HBc results, there is still a need for increasing the test's specificity.

SUMMARY OF THE INVENTION

In an attempt to improve the production of a high-quality, highly purified recombinant antigen for use in diagnosis of anti-HBc antibodies in biological samples, HBcAg was expressed in yeast. The highly purified recombinant protein was characterized and its suitability as a diagnostic antigen was evaluated, by way of example, in a new sandwich enzyme immunoassay (EIA) in which anti-HBc antibodies were captured by binding to recombinant HBcAg on a solid phase and then detected by using recombinant HBcAg labeled with an appropriate marker.

As explained hereabove, assays for the diagnosis of the potential presence of HBV in a patient, as indicated by the presence of anti-HBc antibodies, are known in the art. However, it is believed that such assays are not sufficiently sensitive and specific and a need exists for the production of a high-quality recombinant HBcAg allowing the development of reliable tests, in particular sandwich assays.

Consequently, the subject of the present invention is a new expression system or cassette which is functional in a cell derived from a yeast selected from the group consisting of strain Pichia and Schizosaccharomyces, especially selected from the group consisting of *Pichia pastoris, Pichia methanolica* and *Schizosaccharomyces pombe* and allowing the expression of HBc DNA or fragments thereof encoding HBcAg or fragments thereof, placed under the control of the elements necessary for its expression. A large number of these cells are commercially available in collections such as ATCC (Rockville, Md., USA) and AFRC (Agriculture and Food Research Council, Norfolk, UK). For the purpose of the present invention, said cell may be of the wild type or mutant type. The expression cassette according to the invention comprises elements necessary for the expression of HBcAg or fragments thereof in the considered cells. <<Components necessary for the expression>> is understood to mean all the elements which allow the transcription of a DNA or DNA fragment into mRNA and the translation of the latter into protein. Among these, the promoter region is of special importance. The promoter region may be autologue, i.e, the promoter region of the C-gene of HBV or heterologue, i.e, the promoter region may corresponds to a promoter of a plasmid or promoter of a gene in the host cell. It can be constitutive, that is to say it can allow a constant transcription level during the entire cell cycle. However, it may be advantageous to use a regulable promoter region which makes it possible to vary the transcription levels according to the culture conditions or the cell growth phase depending on the presence of an inducer (activation of transcription) or of a repressor (repression). Generally, the regulable promoter regions are derived from regulable genes for which the regulation mechanisms may be highly varied. On the other hand, an expression cassette according to the invention may, in addition, contain other elements which contribute to the expression of the DNA or fragments thereof as well as transcription activation sequences.

The present invention is also directed to a vector comprising an expression cassette of the present invention. It may be a replicating plasmid vector before integration of DNA or fragments thereof It may be a multicopy vector present between about 1 and 500 copies, preferably between 1 and 20 copies, in the host cell. There may be mentioned, by way of exemple, the vectors derived from pPIC3.5K (Invitrogen).

The present invention also relates to a yeast cell selected from the group consisting of cells of strains Pichia and Schizosaccharomyces, especially selected from the group consisting of *Pichia pastoris, Pichia methanolica* and *Schizosaccharomyces pombe*, and comprising an expression cassette of the invention either in a form integrated into the cell genome or inserted into a vector.

The present invention also embraces the recombinant HBcAg or fragments thereof produced by an expression cassette, a vector or a cell according to the invention. Within the framework of the present invention, HBcAg or fragments thereof may be modified in vitro, especially by addition or deletion of chemical groups, such as phosphates, sugars or myristic acid so as to enhance its stability or the presentation of one or more epitope(s).

The present invention also relates to use of the recombinant HBcAg or fragments thereof of the present invention in diagnosis of anti-HBc antibodies in samples to be tested. With respect to recombinant HBcAg expressed in procaryote cells, such as *E. coli* cells, the recombinant protein or fragments of the present invention is particularly interesting because it is produced in a highly purified form and does not need additional and time consuming steps of purification because the protein is folded, that means close to the native form. Consequently, a test using the protein of the present invention in diagnosis of anti-HBc antibodies in a sample to be tested is more reliable, more specific and more sensitive. The protein of the present invention is particularly attractive in the sandwich method. In the following examples, comparison is made between HBcAg expressed in *E. coli* cells and HBcAg expressed in Pichia, when used in diagnostic test.

Thus the present invention relates to a reagent for the detection and/or the monitoring of an HBV infection, which comprises, as reactive substance the recombinant protein or fragments thereof of the present invention. The above reagent is or will be attached directly or indirectly onto an appropriate support. The support may be, without limitation, in the form of a cone, a tube, a well, beads or the like. The term <<solid support>> as used here includes all materials on which a reagent may be immobilized for use in diagnostic tests. Natural or synthetic materials, chemically modified or otherwise, can be used as solid support, especially polysaccharides such as cellulose materials, cellulose derivatives; polymers such as polystyrene, polyacrylate, polyethylene, vinyl chloride or copolymers such as propylene and vinyl chloride polymer, vinyl chloride and vinyl acetate polymer; styrene-based copolymers; natural fibers and synthetic fibers. Preferably, the support is a polystyrene polymer or a butadiene-styrene copolymer. The attachment of the reagent onto the solid support may be performed in a direct or indirect manner. All techniques for the attachment of a reagent onto a solid support are well known.

The present invention also relates to a process for the detection of anti-HBc antibodies in a biological sample to be tested, such as blood, plasma or serum, from an individual or from an animal likely to be or to have been infected by HBV according to which at least the following steps are performed:

a mixture is prepared comprising:
(i) a reagent as defined above which is or which will be immobilized on a solid support,
(ii) the sample to be tested comprising if they are present anti-HBc antibodies,
(iii) a labeled ligand which will be capable to react with the sample anti-HBc antibodies;

the mixture is incubated for a predetermined time;

the solid phase is separated from the liquid phase; and the possible presence of anti-HBc antibodies is revealed by measuring the level of labeling in the solid phase.

This process named <<sandwich assay>> may be performed in one or further step(s) and the ligand is either a labeled recombinant HBcAg of the present invention or a labeled anti-immunoglobulin.

The present invention embraces another process for the detection of anti-HBc antibodies in a biological sample to be tested, such as blood, plasma or serum, from an individual or from an animal likely to be or to have been infected by HBV according to which at least the following steps are performed:

a mixture is prepared comprising:

(i) a reagent as defined above which is or which will be immobilized on a solid support,
(ii) the sample to be tested comprising if they are present anti-HBc antibodies,
(iii) labeled anti-HBc antibodies which will be capable to react with the reagent;
the mixture is incubated for a predetermined time;
the solid phase is separated from the liquid phase; and
the possible presence of anti-HBc antibodies is revealed by measuring the level of labeling in the solid phase.
This process is named <<competition assay>>.

Because HBcAg is a very powerful immunogen inducing strong humoral response, the recombinant HBcAg of the present invention is used for the production of monoclonal or polyclonal antibodies or fragments thereof obtained by the immunological reaction of an animal organism, preferably a mouse, a rat or a rabbit to an immunogenic agent consisting of the recombinant HBcAg or fragments thereof of the present invention. The production of polyclonal and monoclonal antibodies forms part of the general knowledge of persons skilled in the art. By way of reference, mention may be made of Köhler G. and Milstein C. (1975) and Galfre G. et al. (1977) for the production of monoclonal antibodies and Roda A., Bolelli G. F. (1980), for the production of polyclonal antibodies. Antibodies can also be produced by immunizing mice, rat or rabbit with the HBcAg or fragments thereof of the present invention. For the production of monoclonal antibodies, the immunogene can be coupled to Keyhole Limpet haemocyanin (KLH peptide) as a support for the immunization, or to serum albumin (SA peptide). The animals are subjected to an injection of immunogene using complete Freund's adjuvant. The sera and the hybridoma culture supernatants derived from the immunized animals are analysed for their specificity and their selectivity, using conventional techniques such as, for example, ELISA assays or Western Blot. The hybridomes producing the most specific and the most sensitive antibodies are selected. Monoclonal antibodies can also be produced in vitro by cell culture of the hybridomes produced or by recovering ascites fluid after intraperitoneal injection of the hybridomes into mice. Whatever the method of production, by supernatant or by ascites, the antibodies are then purified. The purification methods used are essentially ion exchange gel filtration and exclusion chromatography or affinity chromatography (protein A or G). A sufficient number of antibodies are screened in functional assays in order to identify the most effective antibodies. The in vitro production of antibodies, of antibody fragments or of antibody derivatives, such as chimeric antibodies produced by genetic engineering, is well known to persons skilled in the art.

More particularly, the term "antibody fragment" is intended to mean F(ab)2, Fab, Fab' and sFv fragments (Blazar et al., (1997) and Bird et al., (1988,)) of a native antibody, and the term "derivative" is intended to mean, inter alia, a chimeric derivative of a native antibody (see, for example, Arakawa et al., (1966) and Chaudray et al., (1989)).

The monoclonal or polyclonal antibody thus obtained is incorporated into a diagnostic composition which is used in a method for detecting at least the HBc protein in a biological sample after pretreatment, if necessary, of the sample to disrupt the cells and release the HBc protein, according to which the biological sample is brought into contact with said diagnostic composition under predetermined conditions which allow the formation of antibody/antigen complexes, and the formation of said complexes is detected. Said composition can also comprise at least one monoclonal or polyclonal antibody or the fragments thereof, directed against HBsAg protein.

The present invention also relates to a sandwich or competition process for detecting at least the HBc protein in a biological sample, if necessary after pretreatment of the sample, to disrupt the cells and release the HBc protein, said processes preferably using at least one monoclonal antibody of the invention.

According to the present invention the sandwich process comprises at least the following steps:
a mixture is prepared comprising:
(i) a reagent which consists of at least one monoclonal antibody of the invention which is or which will be immobilized on a solid support,
(ii) the sample to be tested comprising if it is present HBcAg,
(iii) a labeled ligand which will be capable to react with the sample HBcAg;
the mixture is incubated for a predetermined time;
the solid phase is separated from the liquid phase; and
the possible presence of HBcAg is revealed by measuring the level of labeling in the solid phase. The labeled ligand may be a monoclonal or polyclonal antibody.

In another embodiment of the present invention the sandwich process comprises at least the following steps:
a mixture is prepared comprising:
(i) a reagent which consists of at least one polyclonal antibody of the invention which is or which will be immobilized on a solid support,
(ii) the sample to be tested comprising if it is present HBcAg,
(iii) a labeled ligand which will be capable to react with the sample HBcAg;
the mixture is incubated for a predetermined time;
the solid phase is separated from the liquid phase; and
the possible presence of HBcAg is revealed by measuring the level of labeling in the solid phase. The labeled ligand may be a monoclonal or polyclonal antibody.

According to the present invention the competition process comprises at least the following steps:
a mixture is prepared comprising:
(i) a reagent which consists of at least one monoclonal antibody or polyclonal antibody of the invention which is or which will be immobilized on a solid support,
(ii) the sample to be tested comprising if it is present HBcAg,
(iii) a labeled ligand which will be capable to react with the reagent (i) and which consists of a recombinant HBcAg of the invention;
the mixture is incubated for a predetermined time;
the solid phase is separated from the liquid phase; and
the possible presence of HBcAg is revealed by measuring the level of labeling in the solid phase.

Because HBcAg is a very powerful immunogen inducing strong humoral response the recombinant HBcAg of the invention is usable as an active component of the immune response. Thus, a subject of the present invention is also a vaccine against the HBV virus. This vaccine is prepared according to already known methods used for preparing commercially available vaccines. This vaccine comprises at least the recombinant HBcAg protein of the invention or fragments thereof The recombinant HBcAg protein is obtained by using an expression cassette of the present invention.

An immunogenic or vaccine composition according to the invention is a composition which comprises a recombinant HBcAg protein or a protein fragment as defined above, optionally combined with a suitable vehicle and/or adjuvant and/or a pharmaceutically acceptable excipient. The vaccines comprising the HBcAg protein of the invention, or the fragments thereof, are prepared conventionally and contain an immunoprotective amount of the HBcAg protein, or of the fragments thereof, preferably in a buffered saline solution and mixed or adsorbed using known adjuvants such as aluminium hydroxide or phosphate.

The term "immunoprotective" means that an amount of the recombinant HBcAg protein of the invention or of the fragments thereof which is sufficient to induce a production of antibodies (humoral immune response) which is sufficient to be protective, or a cytotoxic cell-mediated immune response (cellular immune response), to confer a protection against the infectious agent without inducing side effects, is administered to an individual. The two types of response differ in that the antibodies recognize the antigens in their three-dimensional form, whereas the cytotoxic cells recognize portions of said antigens, associated with glycoproteins encoded by the major histocompatibility complex (MHC). Cytotoxic T lymphocytes (CTLs) play an essential role in the defence of cells infected with viruses. They act directly by cytotoxicity, but also by providing specific and nonspecific help to other hematopoietic cells, such as macrophages, B cells and other T cells. The infected cells transform the antigen through intracellular events involving proteases. The transformed antigen is then presented at the surface of the cells, in the form of peptides bound to class I HLA molecules, to the T-cell receptors on the CTLs. Class I MHC molecules can also bind exogenous peptides and present them to CTLs without intracellular transformation. Chisari et al., (Microbiol. Pathogen. 6:31 (1989)) have suggested that the liver lesions could be mediated by a class I HLA-restricted CD8+cytotoxic T-cell response to the antigens encoded by HBV.

The amount of HBcAg protein of the invention or fragments thereof depends on whether adjuvant is added or not, but generally is between 10 and 50 $\mu$g/ml of protein or of fragment. Thus, commonly, 20 $\mu$g/0.5 ml of protein in adults and 10 $\mu$g/0.5 ml in children are administered per dose. The vaccines can also comprise other proteins which enhance the immune response. The HBcAg interacts with certain enhancing proteins, preferably an albumine and/or an unprocessed structural protein from a positive stranded RNA virus, to provide a complex comprised of the HBcAg and the albumin or unprocessed structural protein from the positive stranded RNA virus. Pursuant to such complexing, the HBcAg is believed to undergo conformational changes that enhance the antigenicity of the HBcAg when compared to HBcAg alone in terms of both or either affinity or specificity. The HBcAg protein of the invention, or the fragments thereof, can also be mixed with HBsAg and/or Pre-S proteins or fragments of said proteins, for the formulation of a vaccine. They can also be mixed with hybrid particles carrying epitopes of proteins of other organisms, or with other immunogenic compounds, for the formulation of bivalent or multivalent vaccines. The preparation of vaccines is in particular described in "Vaccines", ed. Voller et al., University Park Press, Baltimore, Md., USA, 1978.

The vaccine is administered at a given dose in one or more intramuscular or subcutaneous injections, followed by (a) booster(s), if necessary. The immunizing effect of the vaccine is monitored by assaying anti-HBc antibodies in the vaccinated individual.

The administration of (a) derived protein(s) or peptide(s) of interest, or the fragment(s) thereof, alone or in combination is used for prophylaxis and/or therapy. These administered proteins or peptides are characterised in that they do not exhibit the virulence of HBV, but are capable of inducing a humoral or cellular immune response in the individual to whom they are administered. Such proteins are termed "modified", but their immunogenicity is conserved.

The identification of (a) vaccine protein(s) or fragment(s) is carried out as follows:

the "modified" candidate molecules are analysed in a functional assay to be sure that they have lost their toxicity and to verify their immunogenicity, (i) by carrying out an in vitro assay of proliferation of CD4+T lymphocytes specific for the antigen administered (T cell assay) or an in vitro assay of cytotoxicity of the CD8+lymphocytes specific for the antigen administered, and (ii) by measuring, inter alia, the level of circulating antibodies directed against the natural protein. These modified forms are used to immunize humans using standardized procedures with suitable adjuvants.

The prepared vaccines are injectable, i.e. in liquid solution or in suspension. As an option, the preparation can also be emulsified. The antigenic molecule can be mixed with excipients which are pharmaceutically acceptable and compatible with the active ingredient. Examples of favorable excipients are water, a saline solution, dextrose, glycerol, ethanol or equivalents, and combinations thereof If desired, the vaccine can contain minor amounts of auxiliary substances such as wetting agents or emulsifiers, agents which buffer pH or adjuvants such as aluminium hydroxide, muramyl dipeptide or variations thereof In the case of the peptides, their coupling to a larger molecule (KLH, tetanus toxin) sometimes increases immunogenicity. The vaccines are conventionally administered by injection, for example intramuscular injection.

The expression "pharmaceutically acceptable vehicle" is intended to mean the supports and vehicles which can be administered to humans or to animals, as described, for example, in Remington's Pharmaceutical Sciences 16th ed., Mack Publishing Co. The pharmaceutically acceptable vehicle is preferably isotonic, hypotonic or is weakly hypertonic with a relatively low ionic strength. The definitions of the pharmaceutically acceptable adjuvants and excipients are also given in Remington's Pharmaceutical Sciences mentioned above.

The present invention also relates to a pharmaceutical composition intended for the treatment or for the prevention of a HBV infection in an individual or animals, comprising a therapeutically effective quantity of the expression cassette, the vector or the cell as defined above.

Finally, the present invention concerns a process for the vaccination of an individual (human or animal) according to an active immunotherapeutic composition, especially a vaccinal preparation, as defined above is injected to the individual; and a process for the treatment or for the prevention of a HBV infection in which a pharmaceutical composition as defined above is administrated to the individual (human or animal).

The peptide sequence of FIG. 1A corresponds to a sequence subtype adw2, but of course the expression cassette according the invention allows the expression of any genotype or subtype.

The examples below will make it possible to demonstrate characteristics and advantages of the present invention in which the following abbreviations mean:

amu, average mass unit; BMGY, rich standard medium containing glycerol; BMMY, rich standard medium containing methanol; ELISA, enzyme-linked immunosorbent assay; G418, geneticin; HBV, hepatitis B virus; HBcAg, HBV core antigen; HBeAg, HBV e antigen; HBsAg, HBV surface antigen; anti-HBc, antibody to HBcAg; MALDI-TOF, matrix-assisted laser-desorption ionisation-time-of-flight; Mut$^+$, wild-type methanol utilization; Mut$^s$, slower methanol utilization.

EXAMPLES

Figure 1:
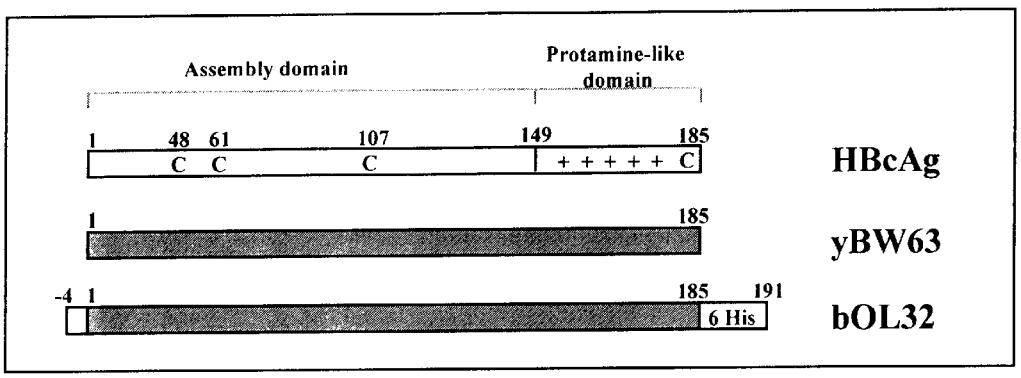
FIG. 1: Schematic representation of the HBcAg amino-acid sequences expressed in *P. pastoris* (yBW63) and in *E. coli* (bOL32). Sequences shown as open lines with the native HBcAg N terminus (residue 1) at the left and the C terminus with its protamine domain (+++) on the right. The two recombinant proteins bOL32 and yBW63 differ through the presence of an additional tetrapeptide (MRGS) at the N terminus and an hexahistidine sequence at the C terminus of bOL32.

1. MATERIALS AND METHODS 1.1. Serum Panels.

All the samples were tested with anti-HBc EIAs: VIDAS HBcT I and II (bioMérieux, Marcy-l'Etoile, France) and IMx Core™ revision 2 (Abbott, Delkenheim, Germany), and with other anti-HBc EIAs including AxSYM Core and Corzyme (Abbott), ORTHO™ HBc ELISA (Ortho clinical diagnostics, Buckinghamshire, UK), Monolisa anti-HBc (Bio-Rad, Hercules, Calif., USA) and Elecsys anti-HBc (Roche Diagnostic, Mannheim, Germany). Other HBV-specific serological markers: HBsAg, anti-HBs, anti-HBc-IgM, HBeAg and anti-HBe, were determined using respectively VIDAS HBsAg, VIDAS anti-HBs T, VIDAS HBc IgM, VIDAS HBe/anti-HBe (bioMerieux) and/or IMx anti-HBe (Abbott) and HBV-DNA PCR (Amplicor HBV Monitor™ test, Roche Diagnostic). IMx Core™ revision 2, AXSYM Core and Elecsys anti-HBc are based on a competitive test principle and include a pretreatment of serum samples with reducing agents in order to minimize false-positive reactions. The detection limit of the VIDAS HBc IgM is 10 PEI units/ml (PEI, Paul Ehrlich Institute, Frankfurt, Federal Republic of Germany). All the assays and PCR amplification were performed and interpreted according to the manufacturer's instructions.

The panel of human sera included 22 negative sera and 20 positive sera. The negative sera were from vaccinated or unvaccinated patients. The negative sera were selected among a large population of blood donors (from Etablissement Francais du Sang, France), the criteria being that they presented discrepant results with the anti-HBc specific commercial EIAs performed (see Table I) except for Nos. 51 and 94. Among them, 17 samples gave false positive or doubtful results only with anti-HBc EIAs which do not include pretreatment of serum with reducing agents (VIDAS HBcT I or II, ORTHO™ HBc ELISA, Monolisa anti-HBc or Corzyme) but they tested negative with the assays including such a treatment such as IMx Core, AxSYM Core and Elecsys anti-HBc. Moreover, after pretreatment of these sera with a reducing agent or addition of anti-IgM, they became negative with the EIAs of the first group (not shown) confirming the presence of reductant sensitive unspecific IgM reactivity as described before (Robertson et al., 1991). The 3 other negative samples tested false positive with some commercial EIAs whether they included pretreatment with reducing agent or not.

The positive panel (Table II) was obtained from blood donors. This panel included one low- positive sample with ORTHO™ HBc ELISA (No. 63) and 3 samples found to be anti-HBc positive with some commercial EIAs but negative for other markers of ongoing or past HBV infection in all the comparative assays performed (see Table II).

For evaluation of the sandwich EIA specificity, a population of 184 HBV-negative serum samples from healthy individuals (voluntary blood donors from Etablissement Francais du Sang, France) was used. Specimens were kept at −20° C. for prolonged storage.

1.2. Construction of an *E. coli* HBcAg Expression Vector, Culture of *E. coli* Transformant and Purification of the Recombinant HBcAg bOL32 by Metal Chelate Chromatography.

The HBV C-gene was PCR amplified from a plasmid containing a copy of the sequence encoding HBcAg (strain adw2) of a HBV strain isolated from an infected patient (E3CB, bioMérieux). The sense primer used 5'ACTG GGATCCATGGACATTGACCCTTATAAAGAA3'(SEQ ID NO: 1) included a BamHI site (underlined) and the start codon of the core gene (boldfaced). The antisense primer used 5'GATCGGAATTCCTAGTGGTGGTGGTGGTGG TGACATTGAGATTCCCG3'(SEQ ID NO: 2) included an EcoRI site (underlined), a stop codon (boldfaced) and a sequence encoding a hexahistidine tail. The purified PCR product was digested with the appropriate enzymes, and ligated to the BamHI-EcoRI sites of the expression vector pMR80 (Cheynet et al, 1993), under the transcriptional control of the tac promoter. The resulting construct pOL032, verified by automated DNA sequence analysis, was used to transform the BL21 *E. coli* strain and the HBcAg protein named bOL32 was expressed in this strain.

A fresh overnight culture of *E. coli* BL21 carrying pOL032 construct was diluted 1:25 in one liter of 2×YT broth (DIFCO) containing 2% glucose (2×YT-G) and ampicillin (100 µg/ml) and grown at 37° C. at a shaking speed of 250 rpm until $D_{600}$ reached 0.9/1.0. The culture was induced by adding isopropyl-β-D-thiogalactopyranoside to a final concentration of 1 mM for 4 hours at 37° C. The culture was then harvested by centrifugation at 6,000 g for 30 min and the cell pellet was frozen at −80° C. until use. The cell pellet was resuspended in 80 ml of lysis buffer [100 mM sodium phosphate/300 mM NaCl (pH 8.0) containing 1 mg/ml lysozyme and protease inhibitor cocktail (Roche Diagnostic Systems)]. After a 30 min incubation at 4° C., 20 µg/ml DNase were added and incubated 30 min at 4° C. Urea (8 M final), 5 mM β-mercaptoethanol and 20 mM imidazole were added to the cell lysate for a final volume of 160 ml and pH was adjusted to 8.0. After complete dissolution, the cell lysate was centrifuged at 10,000 g for 20 min. The supernatant was then incubated with 5 ml of $Ni^{2+}$-nitrilotriacetic acid -Sepharose resin (Qiagen, Courtaboeuf, France) overnight at 4° C. The resin was then packed into a column and washed with 100 mM sodium phosphate, 300 mM NaCl, 6 M Urea, 20 mM imidazole, 5 mM β-mercaptoethanol (pH 7.4) until the $A_{280}$ reached the baseline (approx. 10 column volumes; 60 ml/h). Elution of HBcAg was accomplished with 3 column volumes of buffer containing 50 mM sodium phosphate, 150 mM NaCl, 3 M Urea, 400 mM imidazole, 5 mM β-mercaptoethanol, 20% (w/v) glycerol (pH 7.0). The fractions of interest were collected and dialyzed for 72 hours against a buffer of 50 mM sodium phosphate, 150 mM NaCl, 1 M urea (pH 7.8) containing 2 mM reduced glutathione, 0.2 mM oxidized glutathione and protease inhibitors. The fractions were further dialyzed 48 hours against PBS containing 2 mM EDTA, 20% (w/v) glycerol and protease inhibitors (pH 7.5). The protein content was estimated by using the Bio-Rad protein assay kit, based on the Bradford dye-binding procedure, with BSA as the standard (Bio-Rad).

1.3. Construction of a *P. pastoris* HBcAg Expression Vector, Transformation of *P. pastoris*, Culture Conditions and Fermentation.

The HBV C-gene was PCR amplified by using the plasmid DNA E3CB as a template. The sense primer 5'AGC GGATCCACCATGGACATTGACCCTTATAAAGAATTT GC3'(SEQ ID NO: 3) included a BamHI site (underlined) and the start codon of the core gene (boldfaced) in the context of a Kozac sequence. The antisense primer 5'GATCGGAATTCCTAACATTGAGATTCCCG3'(SEQ ID NO: 4) included an EcoRI site (underlined) and a stop codon (boldfaced). The purified PCR product was digested with the appropriate enzymes, and ligated to the BamHil and EcoRi treated *P. pastoris* expression vector pPIC3.5K (Invitrogen BV, Groningen, the Netherlands). The construct named pBW006 was used to transform the XL1 *E. coli* strain and its DNA sequence was verified.

The plasmid DNA pBW006 was linearized by digestion with SacI to target integration events at the 5'AOXl locus, that encodes alcool oxydase, of the yeast genome by a single crossover event and was used to transform the *P. pastoris* his4 strain GS115 (phenotype His⁻Mut⁻) and the derived his4 aoxl strain KM71 (phenotype His⁻Mut⁻) (Invitrogen) by the spheroplast transformation method (Invitrogen). Stable transformants were selected for histidine prototrophy by plating on minimal dextrose medium [1.34% (w/v) yeast nitrogen base, $6 \times 10^{-5}$% biotin, 1% (w/v) dextrose and 1.5% (w/v) agar] plates without histidine. The His⁺ clones were pooled and further selected for geneticin (G418) resistance by plating them on YPD agar [1% (w/v) yeast extract, 2% (w/v) peptone, 2% (w/v) dextrose and 2% (w/v) agar] plates containing increasing concentrations of G418 (0.25–4 mg/ml) in order to identify those carrying multiple copies of the relevant gene. The resulting His⁺ G418-resistant clones were isolated and plated again on minimal dextrose agar, without histidine and containing G418, to confirm their phenotype.

*P. pastoris* His⁺ G418-resistant transformants were grown in a stirrer flask (250 rpm at 30° C.) in 100 ml of a rich standard medium [1% (w/v) yeast extract, 2% (w/v) peptone, 1.34% (w/v) yeast nitrogen base, 0.4 mg/l biotin and 100 mM potassium phosphate (pH 6.0)] containing 1% (w/v) glycerol (BMGY), until $D_{600}$ reached 2–6. To begin the induction phase, cells were harvested by centrifugation and were resuspended to a $D_{600}$ of 1 in rich standard medium containing 0.5% of methanol (BMMY). Each subsequent day, 100% methanol was added to a final concentration of 1%. On the third day the yeast cells were harvested. Methanol-induced cultures were analyzed for HBcAg expression by using the EIA described below. One transformant, isolated from the parental strain GS115 and able to grow with 1.75 mg/ml G418, was selected for its high level of expression and was retained for fermentation studies.

The following fermentation conditions were used: the dissolved oxygen concentration was maintained above 20% saturation using 40% oxygen-enriched air and a stirring speed of up to 1200 rpm; the pH was maintained at pH 5.0 throughout the fermentation process [with 28% (v/v) ammonium hydroxide], and the temperature was set at 28° C. The transformant was flask grown at 28° C. until $D_{600}$ reached 2–6 in a 100 ml culture BMGY medium. The cells were harvested and used to inoculate a 2 liter bioreactor (Biolaffite-Pierre Guerin S. A., Niort, France) containing 1 liter of BMGY. After exhausting the glycerol from the culture medium, a 50% (w/v) glycerol supply was set at 20 ml/hr/l for 2 hrs. The glycerol supply was then gradually decreased each hour to 10 ml/hr/l, 7.5 ml/hr/l, 5 ml/hr/l, while a methanol supply (100% methanol) was initiated at a rate of 2.7 g/hr/l and then maintained at 5.5 g/hr/l in the culture medium over a 3 day period. To prevent extensive foam formation, antifoam 204 (Sigma) was added. The culture was harvested by centrifugation at 3000 g for 10 min at 4° C., and the cell pellet was recovered and stored at −80° C. until purification.

1.4. Purification of the recombinant HBcAg yBW63 Produced in *P. Pastoris*.

Cell extracts were prepared by vortexing yeast pellet resuspended at 0.2 g/ml (wet yeast biomass) in breaking buffer [50 mM sodium phosphate, 5% (w/v) glycerol, 1 mM PMSF, 1 mM EDTA (pH 7.4)] with acid-washed 425–600 μm glass beads in a bead beater (PolyLabo, Strasbourg, France) in five 1-minute pulses. After disruption, the cell suspension was separated from the glass beads and centrifuged for 20 min. at 10,000 rpm at 4° C. The supernatant was recovered. HBcAg in the supernatant was filtered on 0.22 μm membrane and treated by heating at 65° C. for 60 min. as previously described (Naito et al., 1997). Turbid proteins were removed by centrifugation at 10,000 rpm for 30 min at 4° C., and the supernatant was collected as the HBcAg fraction. The heat purified product was concentrated on a YM3 membrane (cutoff 3,000) in an AMICON cell (Millipore S. A., St-Quentin-Yvelines, France).

1. 5. Sucrose Gradient.

The heat purified yBW63 and the metal chelate purified bOL32 were layered on top of a sucrose gradient formed in polycarbonate tubes [10 ml of 60% (w/v) sucrose, 5 ml of 50% (w/v) sucrose, 5 ml of 40% (w/v) sucrose; 5 ml of 30% (w/v) sucrose and 5 ml of 20% (w/v) sucrose in Tris-HCl 50 mM (pH 7.8)] and spun in a JA25.5 rotor (Beckman Instruments, Gagny, France) at 75,600g for 21 hrs at 4° C. Gradients were fractionated from the top and HBcAg positive fractions were detected by EIA as described below in the 50–60% (w/v) sucrose fractions and were concentrated and dialyzed against a 10 mM phosphate buffer (pH 7.8) in a Vivaspin concentrator (Sartorius S. A., Palaiseau, France) on a 30,000 Da cutoff membrane. The HBcAg concentration was determined by measuring the absorbance at 280 and 320 nm and using the formula: [1.55 $(A_{280}-A_{320})$—0.76 $(A_{260}-A_{320})$] to take into account the presence of nucleic acids entrapped in the core particles (Scheif and Wensink, 1981).

1.6. SDS-PAGE and Western Blot Analysis.

Samples were resolved on 4–12% Bis-Tris Novex Nu-PAGE™ in Nu-PAGE™ MES-SDS running buffer according to the manufacturer's instructions (Invitrogen). The proteins were either stained with Coomassie Brillant blue or were electrophoretically transferred on-to a nitrocellulose membrane Protran (Schleicher & Schuell, Ecquevilly, France). Membranes were blocked with 3% (w/v) BSA in PBS and incubated with a human anti-HBc-positive serum (1:1000 dilution) in PBS containing 0.05% Tween 20 and 1% (w/v) BSA (PBS/BSA/Tween). Goat anti-human IgG horseradish peroxidase conjugate (Jackson Immunoresearch Laboratories, West Grove, Pa., USA) (1:5000 dilution) in PBS/BSA/Tween was used as the secondary antibody.

1.7. Detection of Recombinant HBcAg Reactivity by EIA.

A microtitre plate was coated with a monoclonal anti-HBc antibody (P1D10, bioMérieux, 5 $\mu$g/ml, 100 $\mu$l/well) for 2 hours at 37° C., then saturated with 1% (w/v) milk in PBS. The sample was incubated at a 1:100 dilution in PBS/Tween (100 $\mu$l/well) for one hour at 37° C. After three washes, a human anti-HBc-positive serum (1:1500 in PBS/Tween) was applied for one hour. After three washes a goat anti-human IgG horseradish peroxidase labeled conjugate (Jackson) (1:15000 in PBS/Tween) was incubated for 30 min at room temperature. After further washing, 100 $\mu$l of O-phenylenediamine dihydrochloride colour-development reagent (bioMérieux) were added to each well for 10 min at room temperature. The reaction was stopped by adding 50 $\mu$l of 1.8 N sulfuric acid and the absorbance was read at 492 nm

1.8. N-terminal Sequencing.

Purified HBcAg was resolved by SDS-PAGE in reducing conditions, transferred on-to PVDF membrane and visualized by Ponceau S (Sigma-Aldrich, St Quentin Fallavier, France) staining. Protein bands were excised and subjected to Edman's N-terminal sequence analysis on a protein sequencer (model 492, Applied Biosystems, les Ulis, France).

1.9. Enzymatic "in gel" Digestion of HBcAg and Peptide Analysis.

Purified HBcAg was resolved by SDS-PAGE and the band corresponding to the monomer form was digested in gel. In short, 30 $\mu$g of reduced HBcAg were loaded into gel lanes. Proteins were then identified by Coomassie Brillant blue staining, excised, destained in acetonitrile/ 100 mM ammonium carbonate (pH 8.5) (50:50, v/v) and dried in a vacuum concentrator. Proteins were reduced and alkylated by incubation in 100 $\mu$l of 10 mM DTT/ 100 mM ammonium carbonate (pH 8.5). After a 30 min incubation at 37° C., 100 $\mu$l of 50 mM iodoacetamide/ 100 mM ammonium carbonate (pH 8.5) were added and incubated for another 30 min. The bands were then washed twice with 300 $\mu$l of ammonium carbonate buffer and once with 300 $\mu$l of acetonitrile/ ammonium carbonate buffer (50:50, v/v) before drying. Proteolytic digestion was run by incubating gel pieces with 50 $\mu$l of 25 mM bicarbonate buffer, 1 mM $CaCl_2$ (pH 8.5) containing trypsin (enzyme/substrate, 1:50, w/w) for 18 hrs at 37° C. (Roche Diagnostics). Supernatants were subsequently pooled with those obtained after two further extractions with water/acetonitrile/formic acid (50:50:5 by vol.).

Samples were concentrated and spotted on-to a matrix-assisted laser-desorption ionization-time-of-flight (MALDI-TOF) plate and submitted to molecular-mass analysis on a MALDI-TOF Biflex III (Bruker, Wissembourg, France) mass spectrometer.

1.10. Analysis of Phosphorylation.

HBcAg bOL032 and yBW063 (10 $\mu$g) were resolved on 4–12% Bis-Tris Novex Nu-PAGE™ as described above. To detect phosphorylated proteins, the gel was stained with the Gelcode® phosphoprotein staining kit (Perbio Science, Erembodegen-Aalst, Belgium), following manufacturer's instructions. Phosvitin (10 $\mu$g) and soybean trypsin inhibitor (10 $\mu$g) were used respectively as the positive and negative control phosphoprotein.

1.11. Titration of Free Thiol Groups in the Purified Proteins.

The free thiol group content of each recombinant protein was determined using Ellman's reagent (5,5'-dithiobis-2-nitrobenzoic acid) (Perbio Science). A standard curve was prepared with cysteine hydrochloride monohydrate (Perbio Science) following the manufacturer's instructions. Briefly, 50 $\mu$l of 10 mM Ellman's reagent and 2.5 ml of a 100 mM phosphate buffer (pH 8.0) were added to 100 $\mu$l of standard or sample protein (2.5 mg of HBcAg). After incubation at room temperature for 15 min, the absorbance was read at 412 nm. The thiol concentration was then calculated using the standard curve.

1.12. Electron Microscopy of the E. coli and P. Pastoris-derived HBcAg.

To prepare samples for electron microscopy, the purified proteins (5 $\mu$l of yBW63 at 0.5 mg/ml and 0.8 mg/ml of bOL32) were applied to a 200 mesh copper grids coated with a collodion-carbon film, air dried and then negatively stained with 2% phosphotungstic acid. The particles were examined using a Phillips CM120 transmission electron microscope with an acceleration voltage of 80 kV.

1.13. Detection of HBcAg-nucleic Acids Interactions by Agarose Gel Electrophoresis.

One $\mu$l of RNase A (2477 kunits u/ml, Sigma) or DNase (1 u/ml, Promega) was added to 10 $\mu$l of purified HBc. After incubation for 30 min at 22° C., 2 $\mu$l of loading buffer [50 mM $NaPO_4$, 50% (v/v) glycerin and 0.1% (w/v) bromophenol blue (pH 7.4)] were added, and the sample was loaded onto a 1% (w/v) agarose gel containing ethidium bromide (10 $\mu$g/ml). The gel buffer and electrophoresis buffer was TAE 1X [40 mM Tris-acetate, 1 mM EDTA (pH 8.3)]. The nucleotides were visualized by UV light and the proteins were visualized by Coomassie Brilliant blue staining.

1.14. Detection of Anti-HBc by a Four-step Sandwich EIA.

Magnetic microparticles (Tosyl activated M280 microparticles, Dynal, Oslo, Norway) were coated with E. coli or P. pastoris recombinant HBcAg (6 $\mu$g HBcAg per mg of magnetic microparticles) following the manufacturer's recommendations. The beads were subsequently incubated with a blocking solution [100 mM Tris-HCI, 150 mM NaCl, 2% (w/v) BSA (pH 7.5)] and stored until use at 4° C., as a 1% (w/v) suspension in this blocking solution.

For the assay, 20 $\mu$l of the HBcAg coated beads (already diluted 1:20 in blocking solution) were added to 20 $\mu$l of human serum (1:8 in blocking solution) and 160 $\mu$l of 3 M urea in blocking solution. After a 10 min incubation at 37° C., the beads were subsequently washed four times with 500 $\mu$l of buffer A [50 mM Tris-HCI, 150 mM NaCl, 0.2% Triton X-100, 0.9%o (w/v) sodium azide (pH 8)] and incubated 10 min at 37° C. with 100 $\mu$l of a 1 or 2 $\mu$g/ml solution of biotinylated recombinant HBcAg expressed from E. coli or P. pastoris respectively. After four additional washes in buffer A, the beads were incubated with 100 $\mu$l of a solution containing streptavidine conjugated with alkaline phosphatase, for 10 min at 37° C. After three additional washes, the alkaline phosphatase activity was assayed by adding Lumi-Phos® 530 substrate (200 $\mu$l) (Lunigen, Inc., Southfield Mich., USA) and incubation 10 min at 37° C. The luminescence was measured with a luminometer Leader 450i (Gene-probe, San Diego, Calif., USA).

Results were first expressed as a ratio between the sample signal and reference signal (s/r). The reference serum corresponds to 0.5 PEI units per ml. The optimal s/r cutoff was set to 3.0 for the assay performed with recombinant yBW63 and 2.6 for the assay performed with bOL32 according to the best sensitivity/ specificity balance. A sample was considered positive if it had an s/r greater than or equal to the cutoff value.

2. RESULTS 2.1. Expression of HBcAg in *E. coli* and Purification.

The protein bOL32 (SEQ ID NO: 6), corresponds to the amino acids 1–185 of the HBc sequence subtype adw2, already described by Valenzuela et al., 1980, followed by six histidine residues in C-terminal and four additional amino acid residues in N-terminal due to the cloning strategy (FIG. 1). BOL32 was expressed in *E. coli* and purified under denaturing conditions using the metal-chelate chromatography procedure described in the Materials and Methods section.

In preliminary experiments, the *E. coli* expressed HBcAg could not be bound on metal-chelate column in native conditions. The protein had to be denatured by using 8 M urea and β-mercaptoethanol to allow binding on to the column, which suggests that, in native conditions, the C-terminally located hexa-histidine tag was not accessible. In order to increase the yield of protein renaturation/reoxydation, the metal-chelate purified protein was subjected to dialysis against a folding buffer containing a nondenaturing concentration of urea and reduced/oxidized glutathione as an "oxido-shuffling" system and finally stored in a urea free buffer containing glycerol (see the Materials and Method section). Addition of glycerol in the storage buffer was required as a stabilizing additive to avoid precipitation of the recombinant protein. This presumably <<renatured>>protein was obtained with a yield of 25 mg HBcAg per litre of initial *E. coil* culture and further purified by sedimentation on a sucrose gradient as described in the Materials and Methods section. The final yield after this second purification was approximately 2.5 mg/l of initial *E. coli* culture.

2.2. Expression of HBcAg in *P. Pastoris* and Purification.

The protein yBW63, corresponding to the full HBc sequence (FIG. 1), was expressed in *P. pastoris* using the expression vector pPIC3.5K such that the expression of the gene was under the control of the methanol-inducible alcohol oxidase (AOX1) promoter. HBcAg yBW63 was purified by heat treatment followed by a sucrose gradient as described in the Materials and Methods section. The final yield after this two-step purification was approximately 50 mg/l of initial *P. pastoris* culture.

2.3. Characterization of Recombinant HBcAg From *E. coli* and *P. pastoris*.

Figure 2:
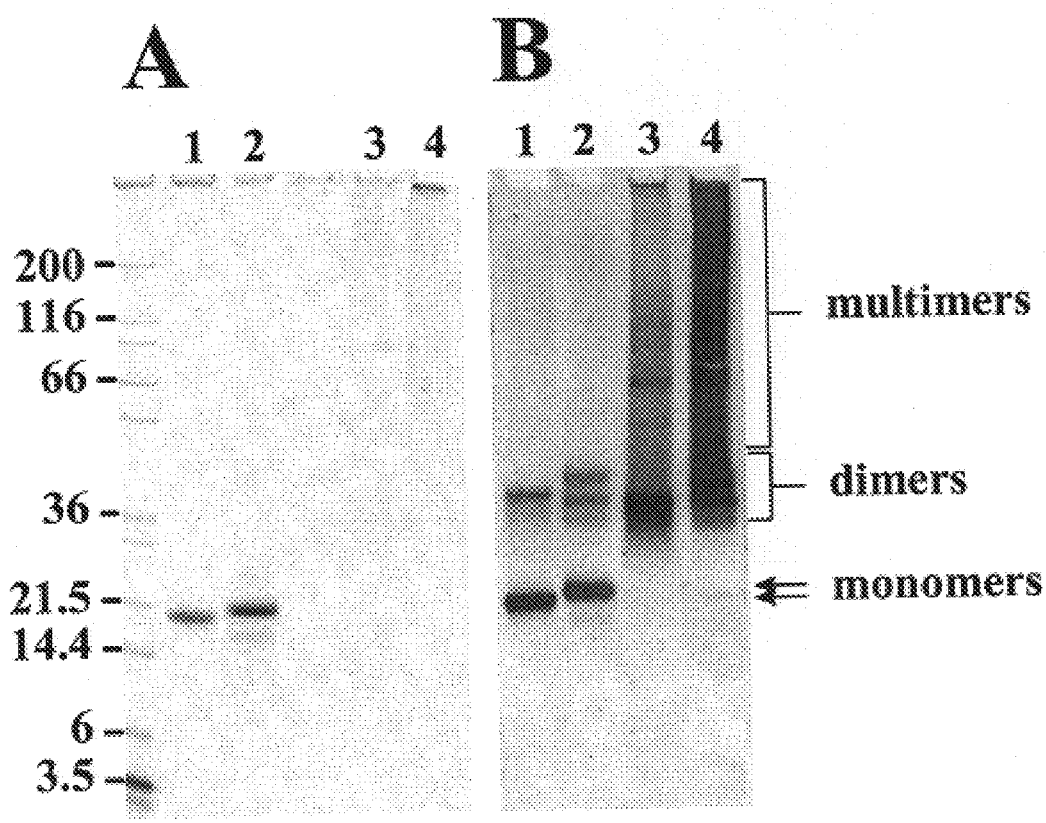
FIG. 2: SDS-PAGE analysis of recombinant HBcAg expressed in *E. coli* and *P. pastoris*. Purified recombinant HBcAg, yBW63 (lanes 1 and 3) and bOL32 (lanes 2 and 4), were resolved by SDS-PAGE and visualized by Coomassie Brillant blue staining (A) or immunoblotting using a HBc-positive human serum (B). The samples were reduced (lanes 1–2) or non-reduced (3–4).

The two purified recombinant HBcAg bOL32 and yBW63 were analyzed by SDS-PAGE and Western-blot with anti-HBc specific human serum. FIGS. 2A–B, lanes 1–2 showed that under reducing conditions, both proteins migrated as a major band with an apparent molecular mass of 20–22 kDa close to the theoretical molecular mass of 21395 and 22650 Da expected respectively for the monomeric protein yBW63 and bOLB32. Western blot analysis also indicated the presence of HBcAg with an apparent molecular mass of 40–44 kDa which should correspond to reductant non-sensitive dimer molecules (FIG. 2B, lanes 1, 2). Indeed, it has been shown that HBc molecules associate into dimers and that a disulfide bridge stabilizes the dimeric form but is not required for its formation (Zhou and Standring, 1992). We observed on Coomassie Brillant blue stained gel a faint band above the size expected for the HBc bOL32 monomer in reducing conditions (FIG. 2A, lane 2) and a faint band under the size of the monomer. The lower molecular weight band (16 kDa) was slightly reactive with the human polyclonal anti-HBc and probably corresponds to a limited proteolysis of the C-terminal domain of bOL32, while the higher molecular weight band was non-reactive suggesting that it is a contaminant protein (FIG. 2). As a result, we also observed molecular mass heterogeneity corresponding to dimeric bOL32 molecules (p22–22; p22–16 ; p16–16) (FIG. 2B, lane 2).

Under non-reducing conditions, both recombinant proteins yBW63 and bOL32 failed to enter the gel or migrated in a very broad band with an apparent molecular mass of 40 kDa and higher, consistent with the presence of dimers stabilized by inter-chain disulfide bonds and higher multimers. These results are in agreement with earlier reports, showing that the majority of HBcAg polypeptides self-assemble into capsid-like particles composed of dimer molecules stabilized by intermolecular disulfide linkages (Zheng et al., 1992).

From freshly prepared *E. coli* expressed HBcAg samples, directly after metal chelate chromatography, we observed predominantly monomeric forms with non-reducing SDS-PAGE. The proportion of dimers and higher multimers increased with storage time (not shown) suggesting a time-dependent increase of intermolecular disulfide-linked molecules. To limit batch to batch variations, we introduced a dialysis in an "oxido-shuffling" buffer into the *E. coli* expressed HBc purification protocol to favor the folding and the self assembly of HBc molecules in capsid-like particles before storage (see Materials and Methods section).

2.4. N-terminal, Molecular Mass, co- or Post-translational Modification.

The two monomeric recombinant proteins were isolated from SDS-PAGE and submitted to N-terminal amino acid sequencing. Edman sequencing analysis indicated that the first five amino acids of bOL32 were Met-Arg-Gly-Ser-Met (SEQ ID NO: 5) which corresponds to the expected N-terminal sequence (FIG. 1). The yBW63 N-terminal sequence could not be determined using the same procedure suggesting blocked N-terminus or N-terminal modification.

In order to confirm the sequence of the two recombinant proteins we used proteolytic degradation with trypsin followed by MALDI-TOF-MS analysis. We carried out in-gel digestion with trypsin of the reduced and alkylated (carboxyamidomethylated-cystein) recombinant proteins. The resulting peptides were detected by MALDI-TOF-MS. All the peptides related to the bOL32 protein matched with the theoretical molecular mass of the expected sequences which enables verification of the first 153 amino-acid residues of bOL32. However, the C-terminal arginine-rich sequence 150–185 could not be verified. Indeed, the masses of the trypsin digestion induced fragments were under the range of our MALDI-TOF-MS (500 amu). Analysis of the yBW63 proteolytically trypsin-derived fragments enables verification of the amino-acid sequence 8–149. As for the bOL32 protein, the C-terminal arginine-rich sequence 150–185 could not be identified. Moreover the N-terminal peptide with or without the first methionine (aa 1–7 or 2–7 with respective theoretical mass 881.4 or 750.4) was not found but a peptide of mass 923.4 was detected which should correspond to the peptide N-acetylated aa 1–7. Conservation of the first methionine is in agreement with the literature showing that methionine aminopeptidase does not act on proteins with large penultimate residues such as aspartic acid (Polevoda et Sherman, 2000). On the other hand, acetylation is described a s one of the most common modification occurring on the vast majority of eukaryotic proteins but rarely on prokaryotic proteins. N-acetylation of the protein yBW63 is not surprising as all eukaryotic proteins starting with Met-Asp (as yBW63) or Met-Glu discovered in literature and data base searches were N-terminally acetylated (Polevoda and Sherman, 2000).

We did not detect any other co- or post-translational modification on the recombinant proteins. By using a specific staining method of phosphorylated proteins directly on SDS-PAGE (described in the Materials and Methods section), we did not show any phosphorylation of the recombinant proteins bOL32 and yBW63 (not shown). These results confirmed those obtained by Machida et al. (1991) showing that HBcAg proteins expressed in E. coli and yeast were not phosphorylated, while core proteins isolated from human tissues as well as recombinant HBcAg expressed in mammalian or insect cells were found phosphorylated on serine residues in the C-terminal domain (Lanford and Notvall, 1990 Liao and Ou, 1995). On the other hand, circular dichroism was used to examine the overall secondary structures of the two recombinant HBcAg capsids and both particles exhibited identical spectra (not shown).

2.5. Free Thiol Groups in the Recombinant HBcAg Proteins.

In order to shed light on the possible similarity or difference between HBcAg bOL32 and yBW63, the presence of free thiol groups in these purified recombinant proteins was evaluated by reaction with Ellman's reagent. Under native conditions, respectively 0.372 and 0.235 measurable sulfhydryl groups per monomeric HBcAg protein bOL32 and yBW63 were found.

2.6. Electron Microscopy of the yBW63 and bOL32 Particles.

Figure 3:
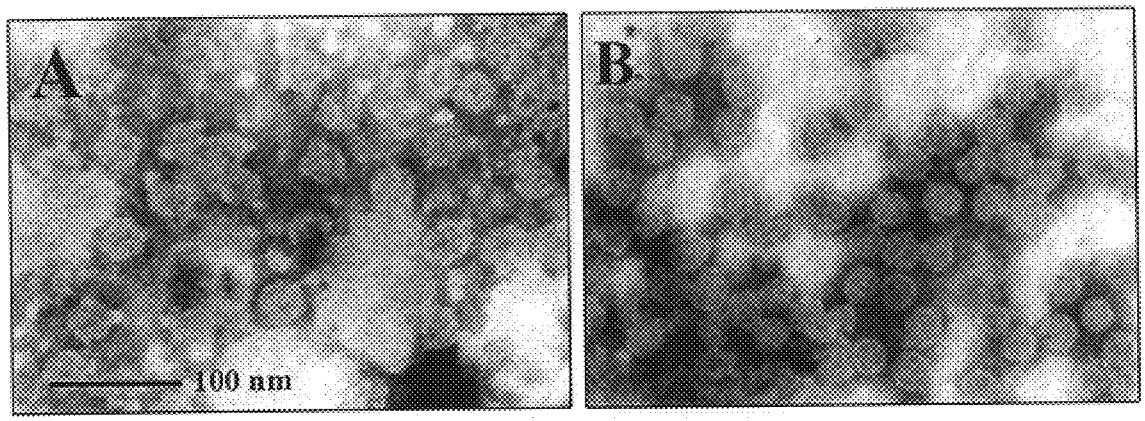
FIG. 3: Electron microscopy showing purified particles assembled from HBcAg proteins yBW63 (A) or bOL32 (B). The purified particles were subjected to electron microscopic examination after negative staining. The bar in the micrograph represents 100 nm.

By electron microscopy, the bOL32 particles exhibited a spherical native-like particle shape averaging 34±2 nm in diameter and the yBW63 particles 28±2 nm (n15 particles) (see FIG. 3).

2.7. Core-nucleic Acids Interactions.

Figure 4:
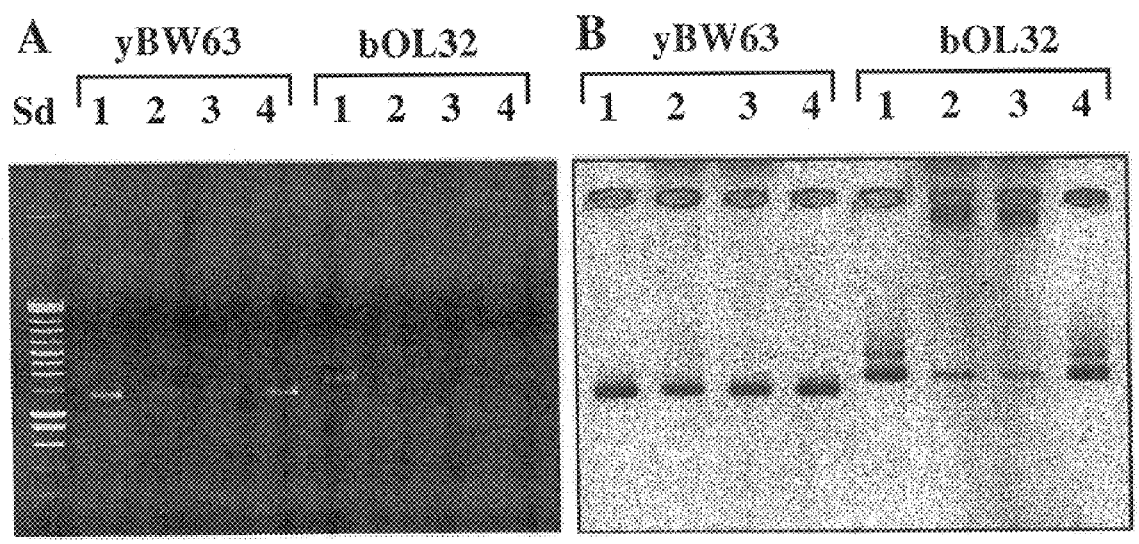
FIG. 4: Analysis of nucleotide-associated core particles by agarose gel electrophoresis. The purified proteins yBW63 and bOL32 were treated with DNase or RNase or with both nucleases and separated by agarose gel (1%, w/v) stained with ethidium bromide (A) or Coomassie Brillant blue (B) Sd, DNA standard Smart ladder (Eurogentec), lane 1, non treated, lane 2, treated with DNase and RNase, lane 3, treated with RNase, lane 4, treated with DNase.

Electrophoresis of the two recombinant HBcAgs on ethidium bromide stained agarose gel followed by Coomassie Brillant blue staining showed that the HBcAg particles, purified either from P. pastoris or from E. coli, contained nucleic acid components (FIG. 4AB, lanes 1). The yBW63 particles migrated as a single band on agarose gel while the bOL32 particles preparation migrated as one major band for which the migration was slightly shorter than the yBW63 migration and two minor bands (FIG. 4B). These discrepancies suggested differences in charge or size between the two preparations consistent with the electron microscopy analysis. Following DNase digestion, the nucleic acids entrapped in the yBW63 or bOL32 particles were unaffected (FIG. 4AB, compare lanes 1 and 4). Following RNase digestion, the nucleic acid components remained associated with yBW63 indicating the presence of DNase protected DNA or RNase protected RNA in the yBW63 capsids. However, the nucleic acid association with bOL32 disappeared following RNase treatment. Moreover, the Coomassie Brillant blue stained agarose gel indicated that degradation of HBc-associated RNA induced a strong modification in the migration of the bOL32 proteins on agarose gel suggesting structural modifications of the HBc particles (FIG. 4B) following RNA release. Presence of RNA and not DNA in the HBcAg particles are in agreement with former results (Birnbaum and Nassal, 1990 ; Zheng et al., 1992).

2.8. Detection of anti-HBc Reactivity in Human Serum.

We set up a sandwich format EIA for the detection of anti-HBc reactivity in human sera. First, the purified recombinant HBcAg, bOL32 or yBW63, was coated on magnetic microparticles as described in Materials and Methods, then the HBcAg coated beads were incubated with human serum (final dilution 1:80 in the presence of 2.4 M urea). After washing, the presence of anti-HBc was revealed by using biotin labeled recombinant HBcAg, homologous to the HBcAg used on the solid phase, followed by a streptavidin-alkaline phosphatase conjugate.

We tested the recombinant HBcAg reactivity against human sera including a panel of 22 negative sera (Table I) and a panel of 20 positive sera (Table II) well characterised by their anti-HBc reactivity with specific commercial EIAs.

With the recombinant protein yBW63, we detected anti-HBc in all the positive specimens while with the protein bOL32 one weak positive serum (No. 63) was not detected (Table II). Among the negative specimens, selected because they gave false positive results with some commercial EIAs, all were confirmed negative with the sandwich EIA performed with yBW63, including the 17 samples containing reductant sensitive unspecific IgM (Table I). However, samples 86 and 87, found to be false positive with VIDAS HBcT I, were also found to be false positive with bOL32. Among the three samples classified as isolated anti-HBc positive, samples 43 and 46, positive with the commercial EIAs performed, were confirmed positive with the sandwich EIA performed with both recombinant proteins. Sample 98, found to be anti-HBc positive with VIDAS HBcT I and negative with the current anti-HBc ELAs was also found to be anti-HBc IgM positive (25 PEI unit/ml) by the VIDAS HBcM and positive in the sandwich assay performed with both recombinant proteins. Although the clinical significance of detecting anti-HBc in the absence of other HBV markers is uncertain (Luo et al., 1991), this sample is probably false negative with most current commercial assays but anti-HBc isolated and identified by our sandwich assay.

Therefore, the sandwich EIA performed with the protein bOL32 appeared to suffer from a lower sensitivity and specificity than the assay performed with the protein yBW63 as one false negative and two false positive results were obtained using the protein bOL32.

TABLE I

Negative panel, results obtained with the anti-HBc sandwich EIA performed with recombinant HBcAg yBW63 and bOL32.

| | anti-HBc results | | | |
|---|---|---|---|---|
| | commercial EIAS[a] | | Sandwich EIA with | |
| Serum N° | a | b | YBW63 | bOL32 |
| 51, 94 | – | – | – | – |
| 39, 40, 41, 71, 76, 77, 79, 80, 81, 83, 84, 85, 88, 89, 99 | 3– | –, D or + | – | – |
| 86, 87 | 3– | 1–, 1+ | – | + |
| 50 | 3+ | 2–, 1D, 1+ | – | – |
| 70 | 1–, 2+ | 3–, 1+ | – | – |
| 82 | 1–, 1D, 1+ | 1–, 3D | – | – |

Results listed as + positive, – negative or D, doubtful on the basis of the cutoff for each assay.
a, commercial EIA among IMx Core ™, AxSYM Core and Elecsys anti-HBc, i.e. including pretreatment of serum with DTT.
b, commercial EIA among VIDAS HBcT I or II and ORTHO ™ HBc, Monolisa anti-HBc and Corzyme.
[a]When discrepancies were observed concerning the anti-HBc results, the number of positive or negative results obtained with the different anti-HBc commercial EIAs performed was specified.

TABLE II

Positive panel, comparison of HBV serological markers and results obtained with the anti-HBc sandwich EIA performed with recombinant HBcAg yBW63 and bOL32.

| | | anti-HBc results | | | | other HBV specific serological markers | | |
|---|---|---|---|---|---|---|---|---|
| | | commercial EIAs[a] | | sandwich EIA with | | | | |
| Status | serum N° | a | b | yBW63 | bOL32 | HBsAg | anti-HBs | anti-HBe |
| Positive Recovered | 5, 12, 19, 23, 24, 26, 90 | + | + | + | + | – | + | + |
| | 45 | + | + | + | + | – | + | – |
| | 63 | 3+ | 3+ | + | – | – | + | + |
| Positive Chronic | 52 | + | + | + | + | + | – | + |
| | 54 | + | + | + | + | + | + | + |
| | 56, 59, 62, 65, 68, 97 | + | + | + | + | + | – | – |
| HBc Isolated | 43, 46 | + | + | + | + | – | – | – |
| | 98 | 3– | 1+, 1– | + | + | – | – | – |

Results listed as + positive or – negative on the basis of the cutoff for each assay.
a, commercial EIA performed among IMx Core ™, AxSYM Core and Elecsys anti-HBc, i.e. including pretreatment of serum with DTT.
b, commercial EIA performed among VIDAS HBcT I and II, ORTHO ™ HBc ELISA, Monolisa anti-HBc and Corzyme.
[a]When discrepancies were observed concerning the anti-HBc result, the number of positive or negative results obtained with the different anti-HBc commercial assays performed was specified.

To further evaluate the specificity of the sandwich immunoassay developed, a 15 population of 184 serum samples from healthy individuals (blood donors) was tested with the recombinant protein yBW63 (see Table III). With a cutoff set at s/r=3, all of the 184 specimens were identified as negative, their s/r values being much lower than the cutoff (Table III). These results assumed a 100% specificity for the sandwich EIA performed with the protein yBW63.

TABLE III

Anti-HBc reactivity in sera from blood donors (n = 184) using P. pastoris HBcAg yBW63 in a sandwich EIA.

| serum | Sample-to-reference ratio[a] |
|---|---|
| N = 180 | 0.08–0.68 mean value:0.19 |
| n = 4 | 0.75–1.07 |
| known negative No. 51 | 0.17 ± 0.08[b] |
| known positive No. 45 | 20.15 ± 4.45[b] |

[a]cutoff = 3
[b]mean of 15 tests

3. DISCUSSION

It has been previously shown that the basic C-terminal 40 residues of recombinant HBcAg is not required for capsid assembly (Milich et al., 1988; Gallina et al., 1989) but enhances the stability of the capsid. Several groups have described that fusion of heterologous sequences to the C terminus allows in some cases the detection of the heterologous sequences with specific antibodies indicating the outside localization of the foreign epitopes (Borisova et al., 1989; von Brunn et al., 1993; Yoshikawa et al., 1993). Since the HBc capsids contain holes on their particulate surfaces (Bottcher et al., 1997; Conway et al., 1997), it was speculated that the foreign polypeptide chains emerged through the holes thus becoming localized on the surface and accessible to antibodies. Therefore, we thought that a C-terminal hexa-histidine tag would be less damageable to the HBcAg structure and more exposed on the particle surface than a N-terminal extension previously described as being surface inaccessible (Karpenko et al., 1997). However our results showed that the C-terminal hexa-histidine tag could not be reached for purification purpose at the surface of the undenatured particles and was probably located within the capsid shell as suggested by Wingfield et al. (1995) or alternatively not accessible in E. coli expressed misfolded structures.

Zheng et al. (1992) have shown that disulfide bond formation is not essential for the assembly of HBcAg capsid. It is a maturing process; the protein initially assembled in the reducing environment of the E. coli cytoplasm is probably fully reduced, but during isolation and storage, oxidation occurs, especially involving highly reactive C-terminal cysteines. Our results obtained with the E. coli expressed HBc are mainly in agreement with these observations showing that HBc purified under denaturing and reducing conditions could reform nucleocapsids by taking advantage of the self-assembly properties of HBcAg.

HBcAg has four cysteine residues, thus a large number of potential disulfide bonding patterns are possible. No intra-chain disulfide bonds exist but two or three inter-chain disulfide bonds can occur (Zheng et al., 1992). Cys183 residue is always involved in a disulfide bond with another Cys183, resulting in the formation of a dimer. These dimers pairs are linked by homologous intermolecular disulfide bridges between two Cys61 residues (Zheng et al., 1992). Cys107 exists as a free sulfydryl buried within the particle structure and not reactive under nondenaturing conditions while Cys48 may participate in disulfide bonding between the same monomers as those linked by Cys61s and exists both as a disulfide and as a free sulfydryl in approximately equal amounts (Zheng et al., 1992). The proportion of free sulfhydryl groups that we measured per HBcAg monomer bOL32 and yBW63 (0.372 and 0.235 respectively) was lower than that found by Zheng et al. (1992). Moreover, we observed that the nucleic acids entrapped with the yBW63 particles were protected better than those associated with bOL32 particles. These results suggest that additive disulfide bonding in yBW63, probably involving Cys48s, could contribute to a further stabilization of the HBcAg particles and explain the higher stability of the yBW63 particles that we observed compared to the bOL32. Alternatively, the C-terminal hexahistidine and/or the N-terminal extension of bOL32 could involve an increase of the size of the holes which penetrate the assembled particle protein shell (Crowther et al., 1994) allowing RNase accessibility to HBc-associated RNA.

Native hepatitis B virus core particles from human liver visualized by negative staining have been reported to have diameters of 27–30 nm and an icosahedral appearance (Onodera et al., 1982). Similar dimensions and morphologies have also been reported for recombinant capsids produced in E. coli (Winfield et al., 1995) or eukaryotic cells (Yamaguchi et al., 1988; Zhou and Strandring, 1991) and have been confirmed by electron microscopy (Crowther et al., 1994). Observation of the yBW63 particles expressed in P. pastoris are in agreement with a 28±2 nm diameter while the bOL32 particles appeared slightly bigger with a 34±2 nm diameter. This difference could be caused by the sequence modifications introduced in the bOL32 construct (4 aminoacids added in N-terminal and 6 histidines in C-terminal).

The overall discrepancies observed between the HBcAg bOL32 and yBW63 (difference in RNase accessibility, amount of free sulfydryl groups, particle size) were associated with differences in the performances of these proteins as a major component in the sandwich EIA developed. The E. coli protein bOL32, compared to the yeast protein yBW63, provided lower sensitivity and specificity. This could be due to incomplete in vitro folding of bOL32 after its denaturing purification process which is suggested by the higher proportion of free thiol groups found for bOL32 compared to yBW63. Moreover, the presence of remaining E. coli contaminant protein in the bOL32 preparation as assessed by FIG. 2 could explain the lower specificity of bOL32.

However, HBcAg expressed in P. pastoris enabled the production with a high yield (50 mg/l of initial P. pastoris culture) of high-quality recombinant HBcAg allowing the development of an anti-HBc sandwich EIA which, unlike competitive EIA, avoid the use of anti-HBc. Preliminary results indicate that this assay could reduce the frequency of false positive results resulting from interfering substances in human sera observed with some commercial EIAs (see Table I). The sandwich assay could also avoid false negative results which could be explained by the presence of antibodies against non-immunodominant epitopes (see table II). Indeed, current inhibition or competition format assays are based on observation regarding the presence of an immunodominant epitope on HBcAg. However, other minor epitopes have been described (Salfeld et al., 1989; Pujol et al., 1994 ; Pusko et al., 1994). We could therefore speculate that the use in the current inhibition assay of anti-HBc directed against the immunodominant epitope is able to mediate in some cases only a partial inhibition of binding of human serum containing antibodies against non immunodominant epitope in a competitive EIA and therefore involve a false negative result.

References

Arakawa et al., 1966, J. Biochem 120: 657–662.
Bird et al., 1988, Science 242: 423–426.
Birnbaum, F. and Nassal, M. 1990. Hepatitis B virus nucleocapsid assembly: primary structure requirements in the core protein. J. Virol. 64:3319–3330.
Blazar et al., 1997, Journal of Immunology 159: 5821–5833 and Bird et al., 1988, Science 242: 423–426.
Borisova, G. P., Berzins, I., Pushko, P. M., Pumpen, P., Gren, E. J., Tsibinogin, V. V., Loseva, V., Ose, V., Ulrich, R., Siakkou, H., and Rosenthal H. A., 1989. Recombinant core particles of hepatitis B virus exposing foreign antigenic determinants on their surface. FEBS Lett. 259, 121–124.
Böttcher, B., Wynne, S. A., and Crowther, R. A., 1997. Determination of the fold of the core protein of hepatitis B virus by electron cryomicroscopy. Nature 386, 88–91.
Chaudray et al., 1989, Nature 339: 394–397.
Cheynet, V., Verrier, B., and Mallet, F., 1993. Overexpression of HIV-1 proteins in Escherichia coli by a modified expression vector and their one-step purification. Prot. Expr. Purif 4, 367–372.
Cohen, B. J. and Richmond, J. E., 1982. Electron microscopy of hepatitis B core antigen synthesized in E. coli. Nature 296, 677–678.
Conway, J. F., Cheng, N., Zlotnick, A., Wingfield, P. T., Stahl, S. J., and Steven, A. C., 1997. Visualization of a 4-helix bundle in the hepatitis B virus capsid by cryo-electron microscopy. Nature 386, 91–94.
Crowther, R. A., Kiselev, N. A., Bottcher, B., Berriman, J. A., Borisova, G. P., Ose, V., and Pumpens, P., 1994. Three-Dimensional structure of hepatitis B virus core particles determined by electron cryomicroscopy. Cell 77, 943–950.
Dodd, R. Y. and Popovsky, M. A., 1991. Antibodies to hepatitis B core antigen and the infectivity of the blood supply. Scientific Section Coordinating Committee [published erratum appears in Transfusion 1991 Sep;31(7):594]. Transfusion 31, 443–449.
Galfre G. et al., 1977 Nature, 266: 550–552.
Gallina, A., Bonelli, F., Zentilin, L., Rindi, G., Muttini, M., and Milanesi, G., 1989. A recombinant hepatitis B core antigen polypeptide with the protamine-like domain deleted self-assembles into capsid particles but fails to bind nucleic acids. J. Virol. 63, 4645–4652.
Karpenko, L. I., Ryazankin, I. A., Chikaev, N. A., Kolesnikova, L. V., and Ilyichev, A. A., 1997. Localization of the amino terminus of the hepatitis B virus core antigen within the core particle. Virus Res. 52, 15–23.
Kenney, J. M., von Bonsdorff, C. H., Nassal, M., and Fuller, S. D., 1995. Evolutionary conservation in the hepatitis B virus core structure: comparison of human and duck cores. Structure 3, 1009–1019.
Köhler G. and Milstein C., 1975: Continuous culture of fused cells secreting antibody of predefined specificity, Nature 256: 495–497.
Lanford, R. E. and Notvall, L., 1990. Expression of Hepatitis B Virus Core and Precore Antigens in Insects Cells and Characterization of a Core-Associated Kinase Activity. Virology 176, 222–233.
Liao, W. and Ou, J. H., 1995. Phosphorylation and nuclear localization of the hepatitis B virus core protein: significance of serine in the three repeated SPRRR motifs. J. Virol. 69, 1025–1029.
Luo, K. X., Zhou, R., He, C., Liang, Z. S., and Jiang, S. B., 1991. Hepatitis B virus DNA in sera of virus carriers positive exclusively for antibodies to the hepatitis B core antigen. J. Med. Virol. 35, 55–59.
Machida, A., Ohnuma, H., Tsuda, F., Yoshizawa, H., Hoshi, Y., Tanaka, T., Kishimoto, S., Akahane, Y., Miyakawa, Y., and Mayumi, M., 1991. Phosphorylation in the carboxy-terminal domain of the capsid perotein of hepatitis B virus: evaluation with a monoclonal antibody. J. Virol. 65, 6024–6030.

Milich, D. R., Chen, M., Schodel, F., Peterson, D. L., Jones, J. E., and Hughes, J. L., 1997a. Role of B cells in antigen presentation of the hepatitis B core. Proc. Natl. Acad. SciUSA94, 14648–14653.

Milich, D. R., McLachlan, A., Stahl, S., Wingfield, P., Thornton, G. B., Hughes, J. L., and Jones, J. E., 1988. Comparative immunogenicity of hepatitis B virus core and E antigens. J. Immunol. 141, 3617–3624.

Milich, D. R., Schodel, F., Hughes, J. L., Jones, J. E., and Peterson, D. L., 1997b. The hepatitis B virus core and e antigens elicit different Th cell subsets: antigen structure can affect Th cell phenotype. J. Virol. 71, 2192–2201.

Naito, M., Ishii, K., Nakamura, Y., Kobayashi, M., Takada, S., and Koike, K., 1997. Simple method for efficient production of hepatitis B virus core antigen in Escherichia coli. Res. Virol. 148, 299–305.

Nassal, M. and Schaller, H., 1993. Hepatitis B virus replication. Trends Microbiol. 1, 221–228.

Onodera, S., Ohori, H., Yamaki, M., and Ishida, N., 1982. Electron microscopy of human hepatitis B virus cores by negative staining-carbon film technique. J. Med. Virol.10, 147–155.

Pasek, M., Goto, T., Gilbert, W., Zink, B., Schaller, H., MacKay, P., Leadbetter, G., and Murray, K., 1979. Hepatitis B virus genes and their expression in E. coli. Nature 282, 575–579.

Polevoda, B. and Sherman, F., 2000. Nalpha -terminal acetylation of eukaryotic proteins. J. Biol. Chem. 275, 36479–36482.

Pujol, F. H:, Bertolotti, A., Fields, H. A., Khudyakov, Y. E., Kalinina, T. I., and Liprandi, F., 1994. A monoclonal inhibition enzyme immunoassay for detection of antibodies against hepatitis B core antigen: confirmation of an immunodominant epitope. J. Immunoassay 15, 239–249.

Pushko, P., Sallberg, M., Borisova, G., Ruden, U., Bichko, V., Wahren, B., Pumpens, P., and Magnius, L., 1994. Identification of hepatitis B virus core protein regions exposed or internalized at the surface of HBcAg particles by scanning with monoclonal antibodies. Virology 202, 912–920.

Robertson, E. F., Weare, J. A., Randell, R., Holland, P. V., Madsen, G., and Decker, R. H., 1991. Characterization of a reduction-sensitive factor from human plasma responsible for apparent false activity in competitive assays for antibody to hepatitis B core antigen. J. Clin. Microbiol. 29, 605–610.

Roda A., Bolelli G. F.: Production of high-titre antibody to bile acids, Journal of Steroid Biochemistry, Vol. 13, pp. 449–454 (1980).

Salfeld, J., Pfaff, E., Noah, M., and Schaller, H., 1989. Antigenic determinants and functional domains in core antigen and e antigen from hepatitis B virus. J. Virol. 63, 798–808.

Schleif, R. F . and Wensink, P. C., 1981. Practicals Methods in Molecular Biology. New York, Springer-Verlag, p. 74.

Spronk, A. M., Schmidt, L., Krenc, C., Pavlis-Jenkins, L., Brady, J., Taskar, S., Angus-Finn, L., and Mimms, L., 1991. Improvements in detection of antibody to hepatitis B core antigen by treating specimens with reducing agent in an automated microparticle enzyme immunoassay. J. Clin. Microbiol. 29,611–616.

Valenzuela, P., Quiroga, M., Zalvidar, J., Gray, P. and Rutter, W. J. 1980. The nucleotide sequence of the hepatitis B viral genome and the identification of the major viral genes Animal Virus Genetics, 57–70, Fields, B. N., Jaenisch, R. and Fox, C. F. (Eds.). Academic Press, New York.

von Brunn, A., Brand, M., Reichhuber, C., Morys-Wortmann, C., Deinhardt, F., and Schodel, F., 1993.: Principal neutralizing domain of HIV-1 is highly immunogenic when expressed on the surface of hepatitis B core particles. Vaccine 11, 817–824.

Weare, J. A., Robertson, E. F., Madsen, G., Hu, R., and Decker, R. H., 1991. Improvement in the specificity of assays for detection of antibody to hepatitis B core antigen. J. Clin. Microbiol. 29, 600–604.

Wingfield, P. T., Stahl, S. J., Williams, R. W., and Steven, A. C., 1995.: Hepatitis core antigen produced in *Escherichia coli*: Subunit composition, conformational analysis, and in vitro capsid assembly. Biochemistry 34, 4919–4932.

Wizemann, H. and von Brunn, A., 1999. Purification of E. coli-expressed HIS-tagged hepatitis B core antigen by Ni2+-chelate affinity chromatography. J. Virol. Methods 77, 189–197.

Wynne, S. A., Crowther, R. A., and Leslie, A. G., 1999. The crystal structure of the human hepatitis B virus capsid. Mol. Cell 3, 771–780.

Yamaguchi, M., Hirano, T., Sugahara, K., Mizokami, H., Araki, M., and Matsubara, K., 1988. Electron microscopy of hepatitis B virus core antigen expressing yeast cells by freeze-substitution fixation. Eur. J. Cell Biol. 47, 138–143.

Yoshikawa, A., Tanaka, T., Hoshi, Y., Kato, N., Tachibana, K., Iizuka, H., Machida, A., Okamoto, H., Yamasaki, M., Miyakawa, Y., and ., 1993. Chimeric hepatitis B virus core particles with parts or copies of the hepatitis C virus core protein. J. Virol. 67, 6064–6070.

Zheng, J., Schodel, F., and Peterson, D. L., 1992. The structure of hepadnaviral core antigens. Identification of free thiols and determination of the disulfide bonding pattern. J. Biol. Chem. 267, 9422–9429.

Zhou, S. and Standring, D. N., 1992. Cys residues of the hepatitis B virus capsid protein are not essential for the assembly of viral core particles but can influence their stability. J. Virol. 66, 5393–5398.

SEQUENCE LISTING

<160> NUMBER OF SEQ ID NOS: 6

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence:sense primer
      including a BamHI site and the start codon of the core gene of HBV

<400> SEQUENCE: 1
actgggatcc atggacattg acccttataa agaa                                34

<210> SEQ ID NO 2
<211> LENGTH: 47
<212> TYPE: DNA
<213> ORGANISM: Artificial Sequence
<220> FEATURE:
<223> OTHER INFORMATION: Description of Artificial Sequence:antisense
      primer including an EcoRI site, a stop codon and a sequence
      encoding a hexahistidine tail

<400> SEQUENCE: 2
gatcggaatt cctagtggtg gtggtggtgg tgacattgag attcccg                  47

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence:sense primer
      including BamHI site and the start codon of the core gene of HBV

<400> SEQUENCE: 3
agcggatcca ccatggacat tgacccttat aaagaatttg c                        41

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence:antisense
      primer including an EcoRI site and a stop codon

<400> SEQUENCE: 4
gatcggaatt cctaacattg agattcccg                                      29

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence:N-terminal
      sequence of recombinant HBcAg bOL32

<400> SEQUENCE: 5

Met Arg Gly Ser Met
 1               5

<210> SEQ ID NO 6
<211> LENGTH: 185
<212> TYPE: PRT
<213> ORGANISM: HBV

<400> SEQUENCE: 6

-continued

```
Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
                180                 185
```

What is claimed:

1. An expression cassette which is functional in a cell derived from a yeast selected from the group consisting of strain Pichia and Schizosaccharomyces, allowing the expression of HBc DNA or fragments thereof encoding HBcAg or fragments thereof, placed under the control of the elements necessary for its expression.

2. The expression cassette according to claim 1, which is functionnal in a cell selected from the group consisting of *Pichia pastoris, Pichia methanolica* and *Schizosaccharomyces pombe*.

3. A vector comprising an expression cassette as claimed in claim 1.

4. A yeast cell selected from the group consisting of cells of strains Pichia and Schizosaccharomyces, especially selected from the group consisting of *Pichia pastoris, Pichia methanolica* and *Schizosaccharomyces pombe*, and comprising the expression cassette as claimed in claim 1.

5. A recombinant HBcAg protein or fragments thereof produced by the expression cassette as claimed in claim 1.

6. A reagent for the detection and/or the monitoring of an HBV infection, which comprises, as reactive substance the recombinant protein or fragments thereof as claimed in claim 5.

7. A process for the detection of anti-HBc antibodies in a biological sample to be tested, such as blood, plasma or serum, from an individual or from an animal likely to be or to have been infected by HBV according to which at least the following steps are performed:

a mixture is prepared comprising:
  (i) a reagent as claimed in claim 6 which is or which will be immobilized on a solid support,
  (ii) the sample to be tested comprising if they are present anti-HBc antibodies,
  (iii) a labeled ligand which will be capable to react with the sample anti-HBc antibodies;

the mixture is incubated for a predetermined time;
the solid phase is separated from the liquid phase; and
the possible presence of anti-HBc antibodies is revealed by measuring the level of labeling in the solid phase.

8. A process for the detection of anti-HBc antibodies in a biological sample to be tested, such as blood, plasma or serum, from an individual or from an animal likely to be or to have been infected by HBV according to which at least the following steps are performed:

a mixture is prepared comprising:
  (i) a reagent as claimed in claim 6 which is or which will be immobilized on a solid support,
  (ii) the sample to be tested comprising if they are present anti-HBc antibodies,
  (iii) labeled anti-HBc antibodies which will capable to react with the reagent;

the mixture is incubated for a predetermined time;
the solid phase is separated from the liquid phase; and
the possible presence of anti-HBc antibodies is revealed by measuring the level of labeling in the solid phase.

9. A process for the production of monoclonal or polyclonal antibodies or fragments thereof, in which an immunogenic agent consisting of the recombinant HBcAg or fragments thereof such as claimed in claim 6 is injected to an animal organism.

10. The process according to claim 9, in which the animal organism is a mouse, a rat or a rabbit.

11. Monoclonal or polyclonal antibody obtained from the process as claimed in claim 10.

12. A process for the detection of HBcAg protein in a biological sample to be tested or from an animal likely to be or to have been infected by HBV according to which at least the following steps are performed:

a mixture is prepared comprising:
(i) a reagent which consists of at least one monoclonal antibody as claimed in claim 11 which is or which will be immobilized on a solid support,
(ii) the sample to be tested comprising if it is present HBcAg, (iii) a labeled ligand which will be capable to react with the sample HBcAg;

the mixture is incubated for a predetermined time;

the solid phase is separated from the liquid phase; and the possible presence of HBcAg is revealed by measuring the level of labeling in the solid phase.

13. The process according to claim 12 in which the labeled ligand is a monoclonal or polyclonal antibody.

14. A process for the detection of HBcAg protein in a biological sample to be tested or from an animal likely to be or to have been infected by HBV according to which at least the following steps are performed:

a mixture is prepared comprising:
(i) a reagent which consists of at least one polyclonal antibody as claimed in claim 11 which is or which will be immobilized on a solid support,
(ii) the sample to be tested comprising if it is present HBcAg,
(iii) a labeled ligand which will be capable to react with the sample HBcAg;

the mixture is incubated for a predetermined time;

the solid phase is separated from the liquid phase; and the possible presence of HBcAg is revealed by measuring the level of labeling in the solid phase.

15. The process according to claim 14 in which the labeled ligand is a monoclonal or polyclonal antibody.

16. An active immunotherapeutic composition, especially a vaccinal preparation, which comprises, as active ingredient, the protein as claimed in claim 5, the active ingredient being optionally conjugated with an immunological support, and optionally a pharmaceutically acceptable excipient and/or excipient and/or diluent.

17. A pharmaceutical composition intended for the treatment or for the prevention of a HBV infection in an individual or animals, comprising a therapeutically effective quantity of the expression cassette as claimed in claim 1.

18. A process for the vaccination of an individual in which the active immunotherapeutic composition as claimed in claim 16 is injected to the invidual.

19. A process for the treatment or for the prevention of a HBV infection in an individual or animals in which the pharmaceutical composition as claimed in claim 17 is administrated to the individual or animals.

* * * * *